United States Patent [19]

Senni et al.

[11] 4,328,154

[45] May 4, 1982

[54] PROCESS FOR THE PURIFICATION OF RAW CAPROLACTAM

[75] Inventors: Paolo Senni; Mario Catoni, both of Colleferro; Domenico Astarita, Segni, all of Italy

[73] Assignee: SNIA Viscosa Societa' Nazionale Industria Applicazioni Viscosa S.p.A., Italy

[21] Appl. No.: 203,367

[22] Filed: Nov. 3, 1980

[51] Int. Cl.³ .......................................... C07D 201/16
[52] U.S. Cl. .............................................. 260/239.3 A
[58] Field of Search ................................. 260/239.3 A

[56] References Cited

U.S. PATENT DOCUMENTS

| | | | |
|---|---|---|---|
| 3,145,198 | 8/1964 | Morbidelli et al. | 260/239.3 A |
| 3,261,467 | 9/1973 | Williams et al. | 260/239.3 A |
| 3,904,609 | 9/1975 | Mattone et al. | 260/239.3 A |
| 3,912,721 | 10/1975 | Mattone et al. | 260/239.3 A |
| 4,036,830 | 7/1977 | De Rooijj et al. | 260/239.3 A |

*Primary Examiner*—Robert T. Bond
*Attorney, Agent, or Firm*—Wenderoth, Lind & Ponack

[57] ABSTRACT

A process for the purification of raw caprolactam obtained by extraction with alkylated phenols from its sulphuric solution, re-extraction with water, oxidation preferably with $KMnO_4$, evaporation of water and distillation, comprises, before the oxidation treatment, a "fast distillation", in the presence of an alkali. The oxidation is conducted at 0°–80° C. and at atmospheric pressure with 0.005–0.5% by weight of $KMnO_4$. The amount of alkali (NaOH) used in the fast distillation is comprised between 0.05 and 0.5% by weight.

9 Claims, No Drawings

PROCESS FOR THE PURIFICATION OF RAW CAPROLACTAM

BACKGROUND OF THE INVENTION

1. Field of the Invention

This invention relates to a process for the purification of raw coprolactam, in particular, of caprolactam obtained by extraction with alkylated phenols from its sulphuric solution. The present invention relates also to the caprolactam thus purified.

2. Prior Art

It is known to extract caprolactam from its sulphuric solution, with alkylated phenols, and to subsequently re-extract the caprolactam with water, from the aqueous phenol solution. The caprolactam thus obtained does not present, however, a purity degree sufficient to permit the obtention of nylon 6 of the "polymerization grade", i.e nylon 6 having the characteristics requested for the production of industrial products (fibers, plastics). Various processes are known for the purification of raw caprolactam thus obtained, whereby a product having such a purity as to be suitable as "polymerization grade" is obtained. As it is well known, these purification treatments comprise oxidizing treatments, for example with potassium permanganate, sodium hypochlorite, ozone, hydrogen peroxide and the like. In order to further increase the degree of purity of the caprolactam, vacuum distillations of the caprolactam are employed downstream of said treatments.

SUMMARY OF THE INVENTION

The Applicant has now surprisingly discovered that the purity degree of the caprolactam may be even further increased by employing, upstream of at least one of the above mentioned oxidation treatments, a "fast distillation" as will be described hereinafter.

The present invention relates, thus, to a process for the purification of raw caprolactam, obtained by extraction with alkylated phenols from its sulphuric solution, re-extraction with water, oxidation treatment (preferably with $KMnO_4$), evaporation of the water and subsequent distillation under a vacuum, characterized in that before the oxidation treatment, a "fast distillation" of the caprolactam in the presence of an alkaline compound is employed in which operation, the evaporated material is substantially not refluxed in the evaporation zone.

DETAILED DESCRIPTION OF THE PREFERRED EMBODIMENTS

A further advantage obtained by applying the process which forms the object of the present invention is that the necessary amount of oxidizing agent is markedly reduced, which leads not only to ecological advantages, but also to economical ones (oxidizing agents saving and less destruction of the caprolactam which is subjected to this treatment, as such oxidizing agents are generally not very selective with respect to the impurities and thus, besides destroying them, decompose a small part of the caprolactam, producing new by-products).

As the alkaline compound, in the presence of which is the fast distillation carried out, sodium hydroxide is preferably employed. The amount of alkaline compound present is suitably varied from 0.05 to 0.5% preferably from 0.1 to 0.4% by weight, with respect to the raw caprolactam. The preferred conditions of the oxidation treatment, which is carried out downstream the "fast distillation" which characterises the present invention, are: a temperature comprised between 0° and 80° C. and atmospheric pressure, preferably a temperature of from 20° to 60° C.

In the preferred case in which potassium permanganate is used as oxidizing agent, the treatment of the caprolactam is suitably effected in the following way: the aqueous caprolactam solution is evaporated to dryness and to the caprolactam residue, aqueous NaOH is added (from 0.005 to 0.5% and preferably from 0.01 to 0.3% by weight of NaOH with respect to the caprolactam) and the whole is subjected to "fast distillation".

The distilled caprolactam is dissolved in water and treated with the above indicated amount of permanganate.

After this treatment, the solution is suitably evaporated to dryness and the raw caprolactam is subjected to the usual distillation treatments, for example to that indicated in U.S. patent application Ser. No. 122,675, filed Feb. 19, 1980 and commonly assigned.

The following Example illustrates and in no way limits the present invention.

EXAMPLE

An aqueous solution of raw caprolactam, constituted by 185.7 parts by weight of water, 100 parts by weight of raw caprolactam, 0.285 parts by weight of o-tert-butylphenol, is dehydrated under a vacuum in a conventional way, 0.3 parts by weight of NaOH are added to it and the solution is evaporated "rapidly" to yield 95 parts by weight of raw distilled caprolactam and 5 parts by weight of raw caprolactam residue. The distilled raw caprolactam is dissolved in 24 parts by weight of water and treated for 30 minutes at room temperature with 0.285 parts by weight of $KMnO_4$. After this period of time the solution is dehydrated under a vacuum whereby a residue consisting of 95.1 parts by weight of raw caprolactam is obtained, which may be further purified according to the process claimed in Ser. No. 122,675, filed Feb. 19, 1980 and commonly assigned.

We claim:

1. In a process for the purification of raw caprolactam obtained by extraction with alkylated phenols from a sulphuric acid solution thereof, re-extraction with water, oxidation treatment, evaporation of the water and subsequent vacuum distillation, the improvement wherein before the oxidation treatment, a "fast distillation", in the presence of an alkaline compound, is employed.

2. The process according to claim 1, wherein the oxidation treatment is performed with $KMnO_4$.

3. The process according to claims 1 or 2, wherein the oxidation treatment is effected at a temperature between 0° and 80° C. and at atmospheric pressure.

4. The process according to claim 3 wherein the temperature is between 20° and 60° C.

5. The process according to claims 1 or 2 wherein amount of $KMnO_4$ employed is between 0.005 to 0.5% by weight.

6. The process according to claim 5 wherein the amount of $KMnO_4$ employed is between 0.01 to 0.4% by weight.

7. The process according to claims 1 or 2 which further comprises evaporating the extracted aqueous caprolactam solution to dryness, adding aqueous NaOH to the caprolactam residue thus obtained, then subjecting the resultant mixture to "fast distillation", recovering the caprolactam from such distillation, dissolving the distilled caprolactam in water and treating same with KMnO₄, evaporating the resultant solution to dryness and then further distilling the caprolactam.

8. The process according to claim 7 wherein the amount of aqueous NaOH solution employed is 0.05 to 0.5% by weight with respect to the caprolactam residue.

9. The process according to claim 8 wherein the amount of NaOH employed is between 0.1 and 0.4% by weight of the caprolactam residue.

* * * * *